United States Patent [19]

Rusin

[11] Patent Number: 5,422,268

[45] Date of Patent: * Jun. 6, 1995

[54] BIOLOGICAL PROCESS FOR RECOVERY OF PLUTONIUM FROM CONTAMINATED SOILS

[75] Inventor: Patricia A. Rusin, Tucson, Ariz.

[73] Assignee: Metallurgiacl and Biological Extraction Systems, Inc., Tucson, Ariz.

[*] Notice: The portion of the term of this patent subsequent to Jun. 22, 2010 has been disclaimed.

[21] Appl. No.: 102,604

[22] Filed: Aug. 5, 1993

Related U.S. Application Data

[63] Continuation-in-part of Ser. No. 852,875, Mar. 17, 1992, abandoned.

[51] Int. Cl.$^6$ .......................... C12S 13/00; B09B 3/00; C01G 56/00
[52] U.S. Cl. .................................. 435/262; 435/262.5; 423/2
[58] Field of Search ...................... 435/262, 262.5, 821, 435/832, 838; 423/2, 20, 27, DIG. 17, 7; 75/712, 744, 715

[56] References Cited

U.S. PATENT DOCUMENTS

| | | | |
|---|---|---|---|
| 4,046,593 | 9/1977 | Au et al. | 134/21 |
| 4,780,238 | 10/1988 | Premugic | 252/184 |
| 5,055,130 | 10/1991 | Arnold et al. | 75/744 |
| 5,221,327 | 6/1993 | Rusin | 75/712 |
| 5,248,329 | 9/1993 | Rusin et al. | 75/715 |

OTHER PUBLICATIONS

Robinson et al. "Microbiol Transformation of Plutonium" Battelle BNL-SA-5531. 1975.

Wildung et al. "Plutonium Interactions with Soil Microbial Metabolites", *Radiation Biochemistry*. vol. 10, No. 19 pp. 1-25. 1987.

J. C. G. Orrow, H. Glathe (1971) "Isolation and Identification of Iron-Reducing Bacteria from Gley Soils" Soil Biol. Biochem. 3:43-55.

Jones, J. Gwynfryn et al. (1983) "Bacterial Reduction of Ferris Iron in a Stratified Eutrophic Lake" Journal of General Microbiology 129:131-139.

Lovley, D. R., E. J. P. Phillips (1986) "Availability of Ferris Iron for Microbioal Reduction in Bottom Sediments of the Freshwater Tidal Potomac River" Applied and Environmental Microbiology 52(4):751-757.

Lovley, Derek R. et al. (1991) "Enzymatic versus Non-enzymatic Mechanisms for Fe(III) Reduction in Aquatic Sediments" Environ. Sci. & Tech. 25(6):1062-1067.

*Primary Examiner*—Michael G. Wityshyn
*Assistant Examiner*—Timothy J. Reardon
*Attorney, Agent, or Firm*—Saliwanchik & Saliwanchik

[57] ABSTRACT

Disclosed is a biological process for recovering plutonium from soils using an iron-reducing bacterium, *Bacillus circulans* NRRL B-21037. A process for obtaining such bacteria is disclosed. The invention process gives upwards of about 88% yield of plutonium from soils. Further, pertinent gene(s) encoding enzymes obtainable from iron-reducing microbes can be used by placing such gene(s) on a suitable vector and transforming a competent host. The transformed host then can be used in the same manner as the native bacterium.

2 Claims, No Drawings

BIOLOGICAL PROCESS FOR RECOVERY OF PLUTONIUM FROM CONTAMINATED SOILS

CROSS-REFERENCE TO A RELATED APPLICATION

This is a continuation-in-part of application Ser. No. 07/852,875, filed Mar. 17, 1992, now abandoned.

BACKGROUND OF THE INVENTION

The recovery of plutonium from contaminated soils is made difficult by the lack of solubility of the plutonium in most aqueous media. Plutonium can become deposited in the soil due to leakage of nuclear waste containers, from scrapping operations of radioactive reactor cores from nuclear submarines, scrapping of nuclear weapons, from irradiated reactor fuels, atomic weapons testing, production of plutonium for nuclear weapons, and nuclear reactors that formerly produced plutonium.

The characterization of the chemical forms of plutonium present in the environment is still the object of intense research. Oxides and hydroxides appear to be representative and common constituents in the soil.

Current methods for the decontamination of soils and their attendant deficiencies are as follows: (1) Burial of wastes in depositories. The cost for transport and long-term storage of contaminated wastes are high and such containers often leak over the long term. (2) Solubilization of plutonium from soil using strong acids such as nitric or nitric/hydrofluoric acid. Such treatment is not practical due to corrosion problems and destruction of the soil matrix. (3) Use of siderophores or chelators alone to solubilize plutonium. Chelators such as EDTA solubilize only small quantities of plutonium. The most efficient siderophore studied thus far, (enterobactin), solubilizes only 20% of the plutonium in 6 days. (4) Volatilization of $PuO_2$ as $PuF_6$. Extremely high temperatures are required and fluorine gas is highly reactive and corrosive making this process expensive. There is no known prior art biological process for the microbial solubilization of plutonium.

BRIEF SUMMARY OF THE INVENTION

The subject invention concerns the use of iron-reducing microbes to recover plutonium from soils. Specifically exemplified is the use of iron-reducing bacteria. Plutonium recovery yields of about 89% have been achieved by use of the subject process.

In one embodiment of the subject process, enzymes obtainable from iron-reducing bacteria can be used in a plutonium recovery process. In this embodiment, isolated enzymes are contacted with contaminated soil to solubilize plutonium.

A further embodiment of the subject process is the use of the gene(s) obtainable from iron-reducing bacteria in a plutonium recovery process. The gene(s) can be inserted into another biological host via a suitable biological vector, e.g., a plasmid. The transformed host can then be used in essentially the same manner as the parent iron-reducing bacteria to recover plutonium from soils.

The biological process of the subject invention is the first known process which can yield up to about 89% plutonium recovery from plutonium oxides and up to 88% plutonium recovery from plutonium-contaminated soil. Thus, the subject process can be termed a landmark achievement in the art of remediating plutonium-contaminated soils.

DETAILED DISCLOSURE OF THE INVENTION

Upon contacting soil contaminated with plutonium with a culture of an iron-reducing microbe, or mutants thereof, for a sufficient time to solubilize plutonium in the soil, separating the microbial culture (liquid) from the residual soil, there is obtained a liquid portion comprising plutonium and other solubilized heavy metals such as iron, and the like. In a preferred embodiment, the microbe is a bacterium. Plutonium is recovered from the liquid portion by standard procedures, e.g., ion exchange processes, solvent extraction processes, precipitation processes, volatility processes, slagging processes, liquid metal processes, and electrolytic processes as described in *Chemistry of Plutonium*, 1979, second printing, by J. M. Cleveland, American Nuclear Society, Ill. Preferably the invention process is conducted under substantially anaerobic conditions. Without iron-reducing bacteria present, plutonium solubilization is <5%. Following biotreatment with the iron-reducing bacteria, plutonium solubilization was about 88%.

Iron-reducing bacteria may include members of the genera Clostridium, Enterobacter, Klebsiella, and Pseudomonas. The identification and isolation of iron-reducing bacterium is readily executed by one of ordinary skill in the art. Iron-reducing bacterium may be isolated from soil samples or ore samples containing iron. Identification of those isolates that reduce iron is accomplished by culturing those organisms on medium supplemented with a common ferric iron source. As an example, Minimum Salts Medium is supplemented with 0.5% Bacto Agar (Difco Laboratories, Detroit, Mich.), 0.18% glucose, and 0.4% goethite ($HFeO_2$). Bacterial reduction of iron in the medium is detected by a color change from rusty orange to colorless. Positive cultures are then further isolated and purified by standard bacterial techniques.

An iron-reducing bacteria, or mutants thereof, which retain the property of reducing iron, can be cultured in any standard biological medium which supports its growth. Many such media are available for culture from Difco, Detroit, Mich. Generally, such a growth medium will contain a carbon source, e.g., glucose or starch, nitrogen source, e.g. peptone, phosphorus, sulfur, trace elements, and growth factors. Preferably the culture medium will contain at least about 0.05M nitrilotriacetic acid (NTA), or a similar chelator, e.g., ethylenediaminetetraacetic acid (EDTA), fluoride, hydroxide, acetylacetone, oxalate, or 1,1,1,-trifluoro-3-2'-thenoylacetone. The chelator stabilizes the iron solubilized by the bacteria. Mutants of the iron-reducing microbes can be made by procedures well known in the art. The mutants can be made using ultraviolet light and nitrosoguanidine by procedures well known in the art.

Iron-reducing bacteria may be able to use fermentative metabolism or anaerobic respiration. The fermentative iron-reducing bacteria will ferment a carbon source such as glucose and use iron as an electron sink for the reoxidation of NAD (nicotinamide adeninc dinucleotide) which is reduced during the fermentative process. Bacteria using anaerobic respiration oxidize a carbon source such as glucose under anaerobic conditions using iron as an electron acceptor in the electron transport chain for the formation of ATP (adenosine triphosphate). Bacterial isolates used to exemplify the claimed process include the following:

Certain of the cultures useful in the subject invention were deposited in the permanent collection of the Patent Culture Collection (NRRL), Regional Research Center, 1815 North University Street, Peoria, Ill. 61604 U.S.A.; or in the American Type Culture Collection (ATCC), 12301 Parklawn Drive, Rockville, Md. 20852. The deposit dates and accession numbers are as follows:

| Isolate | Strain | Accession No. | Deposit Date |
| --- | --- | --- | --- |
| Bacillus polymyxa | D-1 | ATCC 50030 | — |
| Bacillus circulans | SD-1 | NRRL B-21037 | February 8, 1993 |
| Bacillus polymyxa | MBX-10 | NRRL B-21038 | February 8, 1993 |
| Bacillus circulans | MBX-69 | NRRL B-18768 | March 20, 1991 |

D-1 is publicly available as disclosed in U.S. Pat. No. 5,055,130. MBX69, MBX-10, and SD-1 have each been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the culture. The depositor acknowledges the duty to replace a deposit should the depository be unable to furnish a sample when requested, due to the condition of the deposit(s). All restrictions on the availability to the public of the subject culture deposit will be irrevocably removed upon the granting of a patent disclosing them.

Enzyme(s) produced by the iron-reducing microbes of the invention can be recovered from the culture medium of the microbe. The recovery process can be one in which the microbial cells at harvest are lysed and the enzyme(s) recovered from the culture medium by standard procedures. The resulting enzyme preparation can be used to treat contaminated soils to solubilize plutonium and recover plutonium as disclosed herein. The treatment of the soils with an enzyme preparation, as disclosed above, can be by use of columns and other means well known in the enzyme art. The enzyme preparation so used can be in either a crude or essentially pure form.

Novel recombinant microbes can be made by isolating the gene(s) from the iron-reducing microbe by using known procedures, and transforming suitable hosts with the gene(s). The gene(s) encode enzymes which are capable of solubilizing plutonium found in the soil.

A wide variety of ways are available for introducing a gene into a microorganism host under conditions which allow for stable maintenance and expression of the gene. One can provide for DNA constructs which include the transcriptional and translational regulatory signals for expression of the gene, the gene under their regulatory control and DNA sequence homologous with a sequence in the host organism, whereby integration will occur, and/or a replication system which is functional in the host, whereby integration or stable maintenance will occur.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

A marker structural gene is used to provide for the selection of the host microbe which has acquired the desired nucleotide sequence (via, for example, transformation, electropotation, conjugation, or phage mediated). The marker will normally provide for selective advantage, for example, providing the biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene. In this manner, the enhanced expression of a siderophore may provide for a competitive advantage for the host, so that it may effectively compete with wild-type microorganisms.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the gene will be in close proximity to the gene providing for complementation as well as the gene providing for the competitive advantage. Therefore, in the event that a gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the gene, where functional in the host. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system form a virus which is stable in the host.

The gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for solubilizing plutonium found in soils.

Suitable host cells can be Gram-negative bacteria, including Enterobacteriaceae, such as Escherichia, and Pseudomonadaceae, such as Pseudomonas, and fungi.

The recombinant cellular host containing the gene(s) may be grown in any convenient nutrient medium, where the DNA construct provides a selective advantage, providing for a selective medium so that substantially all or all of the cells retain the gene. These cells may then be harvested in accordance with conventional ways.

Following are examples which illustrate procedures, including the best mode, for practicing the invention. These examples should not be construed as limiting. all percentages are by weight and all solvent mixture proportions are by volume unless otherwise noted.

EXAMPLE 1

Isolation of Iron-Reducing Bacteria

Iron-reducing microbes can be readily identified and isolated using standard procedures well known to those skilled in the art. For example, iron-reducing bacteria are isolated by making a slurry of soil;ore, sediment, or water samples in a mineral salts medium supplemented with 0.5% Bacto Agar (Difco Laboratories, Detroit, Mich.), 0.18% glucose, and 0.4% goethite ($HFeO_2$). This medium is called iron medium. The composition of the medium is as follows:

| | |
|---|---|
| $NaHCO_3$ | 2.5 g |
| $CaCl_2 \cdot 2H_2O$ | 0.1 g |
| KCl | 0.1 g |
| $NH_4Cl$ | 1.5 g |
| $NaH_2PO_4 \cdot H_2O$ | 0.6 g |
| NaCl | 0.1 g |
| $MgCl_2 \cdot 6H_2O$ | 0.1 g |
| $MgSO_4 \cdot 7H_2O$ | 0.1 g |
| $MnCl_2 \cdot 4H_2O$ | 0.005 g |
| Distilled $H_2O$ | 1.0 L |

Ten-fold dilutions of soil and ore samples are made into iron medium and all tubes are incubated at 30° C. Microbial reduction and dissolution of iron is detected by a color change from rusty orange to clear. Subsamples from the higher dilutions in which reduction is detected are transferred to trypic soy agar (TSA, Difco) for isolation and purification of the bacteria. Each bacterial isolate is retested in iron medium to confirm its bioreductive activity.

EXAMPLE 2

Culturing Iron-Reducing Bacteria

A subculture of the iron-reducing bacteria can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Nitrilotriacetic acid | 0.1 M |
| Salt Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

An alternative growth medium is potato extract, i.e., potato extracted by heat or enzymatically by standard procedures, supplemented with a chelator, e.g., nitrilotriacetic acid, and the like. Another alternative growth medium is Tryptic Soy Broth.

The above media and procedures can be used with most iron-reducing bacteria and can be readily scaled up to large fermentors by procedures well known in the art.

EXAMPLE 3

Iron-Reducing Bacteria Used To Reduce Plutonium

This example, which discloses the use of various iron-reducing bacteria to reduce plutonium, is merely to exemplify the invention. The invention concerns the use of any iron-reducing bacterium to reduce plutonium. Though iron-reducing bacteria may vary in their effectiveness to reduce plutonium, it is well within the skill of those in this art to determine the optimal use conditions for any iron-reducing bacterium in the invention process. It should be understood that one aspect of the invention is the use of bacteria which can reduce iron. Thus, other metabolic characteristics, e.g., manganese reduction, are not the criteria by which a bacterium is chosen to function in the invention process.

Iron-reducing bacterial isolates were grown to an optical density of $A_{600}=0.075$ (cm$^{-1}$) in standard tryptic soy broth (Difco). Solid hydrous plutonium oxide was added to these bacterial cultures with and without the addition of 0.05M nitrilotriacetic acid (NTA). Cultures were incubated at ca. 22° C. on a rotator. After 48 hours incubation, the solids and liquids were separated by centrifugation. The residual plutonium solids were resuspended in fresh bacterial cultures and incubated in the same manner for 4 more days. At this time, all liquids and residual solids were analyzed individually for plutonium content using a scintillation counter.

Up to 89% of the plutonium was solubilized as follows:

TABLE 1

| Percent plutonium solubilized in 6 days | | |
|---|---|---|
| Isolate | NTA Present | NTA Not Present |
| Bacillus polymyxa D-1 (ATCC 55030) | 89 | not done |
| Bacillus circulans SD-1 (NRRL B-21037) | 87 | 38 |
| Bacillus polymyxa MBX 10 (NRRL B-21038) | 86 | not done |
| Bacillus circulans MBX 69 (NRRL B-18768) | 84 | 35 |
| Tryptic soy broth | 4.5 | 1 |

EXAMPLE 4

Plutonium Solubilization with Bacterial Metabolites

Tryptic soy broth was inoculated with Bacillus SD-1 and incubated for 4 days. The culture was centrifuged and the supernatant sterilized by filtration (0.22 μm, Gelman). The filtrate was amended with PuO$_2$ and incubated for 6 days to test for plutonium solubilization by extracellular products produced by isolate SD-1. After 6 days incubation, the liquid and residual solids were analyzed individually for plutonium content using a scintillation counter.

Data demonstrated that the solubilization of hydrous PuO$_2$ by Bacillus SD-1 takes place in a defined medium in the presence of the bacteria, but does not occur to a significant extent in controls containing metabolites produced by SD-1.

EXAMPLE 5

Biotreatment of Contaminated Soil Samples

The soil tested was contaminated with $^{239}$Pu. Bacteria used were *Bacillus polymyxa* D-1, *Bacillus circulans* SD 1, *B. polymyxa* MBX 10, and *B. circulans* MBX 69. The two growth media used were tryptic soy broth (TSB) and mineral salts medium (MSM). The MSM medium is iron medium in Example 1 with the exception that the goethite is omitted. In each case, soil tests were done with and without 0.05M nitrilotriacetic acid (NTA). All bacteria were grown overnight prior to addition of soil in TSB or MSM at 30° C. Sterile screw-cap tubes with septa were used. Each tube received 4 g±0.2 g of contaminated soil and 47.5 ml bacterial culture. All tubes were incubated on a rotator at 15 rpm at 35° C.

Soil/liquid separation was achieved by centrifugation at 3,000 rpm for 10 minutes. At the end of the extraction process, the residual soil samples were washed three times with centrifugation, dried, and weighed. These solids and samples of the original untreated soil were analyzed for total plutonium by alpha spectroscopy. Results are shown in Table 2.

TABLE 2

| Percentages of $^{238}$plutonium and $^{239,240}$plutonium removed by biological treatments | | |
|---|---|---|
| | $^{238}$Pu % removed | $^{239,240}$Pu % removed |
| SD 1-MSM | 30.79 | 27.54 |
| SD 1-MSM-NTA | 83.40 | 82.75 |
| SD 1-TSB | 87.72 | 88.09 |
| SD 1-TSB-NTA | 81.34 | 77.80 |
| D-1-MSM | 22.99 | 27.29 |
| D-1-MSM-NTA | 78.58 | 82.89 |
| D-1-TSB | 40.08 | 41.27 |
| D-1-TSB-NTA | 83.54 | 83.64 |
| MBX 10-MSM | 12.75 | 14.21 |
| MBX 10-MSM-NTA | 82.52 | 83.98 |
| MBX 10-TSB | 7.87 | 18.05 |
| MBX 10-TSB-MSM | 81.49 | 85.74 |
| MBX 69-MSM | 39.53 | 38.70 |
| MBX 69-MSM-NTA | 76.53 | 81.02 |
| MBX 69-TSB | 18.90 | 18.57 |
| MBX 69-TSB-NTA | 84.64 | 84.21 |

These data show successful extraction of plutonium from contaminated soils.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A process for recovering plutonium from plutonium-contaminated soil which comprises (a) culturing an iron-reducing *Bacillus circulans* SD-1 strain having all the identifying characteristics of NRRL B-21037 in a growth medium; (b) inoculating said soil with an amount of the culture of said SD-1 strain sufficient to solubilize said plutonium and incubating, under substantially anaerobic conditions and in the presence of an amount of a chelator sufficient to stabilize solubilized plutonium, for a sufficient time to solubilize plutonium in said soil to obtain a residue and a liquid portion; and, (c) recovering solubilized plutonium from said liquid portion.

2. The process, according to claim 1, wherein said soil is inoculated with said culture and incubated for about 2 to about 6 days.

* * * * *

UNITED STATES PATENT AND TRADEMARK OFFICE
CERTIFICATE OF CORRECTION

PATENT NO. : 5,422,268

DATED : June 6, 1995

INVENTOR(S) : Patricia A. Rusin

It is certified that error appears in the above-indentified patent and that said Letters Patent is hereby corrected as shown below:

Column 2, line 62: Delete "adeninc" and insert --adenine--.

Column 4, line 31: Delete "electropotation" and insert --electroporation,--.

Signed and Sealed this

Fifth Day of September, 1995

Attest:

BRUCE LEHMAN

Attesting Officer

Commissioner of Patents and Trademarks